(12) United States Patent
Kennedy et al.

(10) Patent No.: US 9,695,286 B2
(45) Date of Patent: Jul. 4, 2017

(54) RUBBERY POLYSILOXANES CARRYING CYANOACRYLATE FUNCTIONS AND RELATED METHODS FOR THEIR PREPARATION AND USES THEREFOR

(71) Applicants: Joseph Kennedy, Akron, OH (US); Istvan Szanka, Balmazujvaros (HU); Amalia Szanka, Budapest (HU)

(72) Inventors: Joseph Kennedy, Akron, OH (US); Istvan Szanka, Balmazujvaros (HU); Amalia Szanka, Budapest (HU)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 15/026,344

(22) PCT Filed: Oct. 8, 2014

(86) PCT No.: PCT/US2014/059643
§ 371 (c)(1),
(2) Date: Mar. 31, 2016

(87) PCT Pub. No.: WO2015/054357
PCT Pub. Date: Apr. 16, 2015

(65) Prior Publication Data
US 2016/0215098 A1 Jul. 28, 2016

Related U.S. Application Data

(60) Provisional application No. 61/888,040, filed on Oct. 8, 2013.

(51) Int. Cl.
| | |
|---|---|
| *C08G 77/388* | (2006.01) |
| *A61K 31/74* | (2006.01) |
| *A61L 24/00* | (2006.01) |
| *A61L 24/04* | (2006.01) |
| *A61L 26/00* | (2006.01) |
| *C08G 77/20* | (2006.01) |
| *C08G 77/22* | (2006.01) |

(52) U.S. Cl.
CPC ............ *C08G 77/388* (2013.01); *A61K 31/74* (2013.01); *A61L 24/001* (2013.01); *A61L 24/046* (2013.01); *A61L 26/0019* (2013.01); *A61L 26/0061* (2013.01); *C08G 77/20* (2013.01); *C08G 77/22* (2013.01)

(58) Field of Classification Search
USPC ...................................................... 528/10–43
See application file for complete search history.

(56) References Cited

U.S. PATENT DOCUMENTS

| | | | | |
|---|---|---|---|---|
| 4,012,402 | A | * | 3/1977 | Buck ..................... C07C 255/00 526/279 |
| 4,013,703 | A | | 3/1977 | Buck |
| 4,254,248 | A | * | 3/1981 | Friends ................. C08F 230/08 351/159.02 |
| 2009/0210002 | A1 | | 8/2009 | Salamone et al. |

FOREIGN PATENT DOCUMENTS

| | | | |
|---|---|---|---|
| JP | 6-100838 A | * | 4/1994 |
| JP | 11-302602 | * | 11/1999 |
| WO | 9415907 A1 | | 7/1994 |

\* cited by examiner

*Primary Examiner* — Marc Zimmer
(74) *Attorney, Agent, or Firm* — Renner Kenner Greive Bobak Taylor & Weber (57) ABSTRACT

A family of silicone rubbers (e.g., polydimethylsiloxane) carrying one or more cyanoacrylate groups and their methods of production are provided. These silicone rubbers endowed with cyanoacrylate groups are useful in a variety of wound care applications, including wound closures, adhesives, sealants and skin protectors. The silicone rubber moiety provides oxygen and moisture permeability (i.e., "breathability"), biocompatibility, optical transparency, and good mechanical properties, while the cyanoacrylate group imparts instantaneous adhesion/attachment to living tissues such as skin on par with that of contemporary cyanoacrylate-based wound care products.

17 Claims, 2 Drawing Sheets

RUBBERY POLYSILOXANES CARRYING CYANOACRYLATE FUNCTIONS AND RELATED METHODS FOR THEIR PREPARATION AND USES THEREFOR

CROSS-REFERENCE TO RELATED APPLICATIONS

This application claims the benefit of U.S. Provisional Patent Application No. 61/888,040, filed Oct. 8, 2013.

TECHNICAL FIELD

The present invention relates to a silicone rubber. More particularly, the present invention relates to a silicone rubber (SiR), such as polydimethylsiloxane (PDMS), endowed or functionalized with one or more cyanoacrylate groups (-CA) so as to create a unique silicone rubber having particularly useful properties not previously found in other silicone rubbers or other compositions functionalized with cyanoacrylates. These cyanoacrylate-functionalized silicone rubbers (SiR-CA) of the present invention are seen as particularly useful as wound closures, adhesives, sealants, and skin protectants. A method for the preparation of the cyanoacrylate-functionalized silicone rubber is also provided.

BACKGROUND FOR THE INVENTION

There are several contemporary cyanoacrylate-based wound closures that exist today, including, for example, Dermabond®, Indermil®, and Histoacryl®. Dermabond® topical skin adhesive (2-octyl cyanoacrylate) is a sterile, liquid skin adhesive that holds wound edges together and is available from Ethicon US LLC, a Johnson & Johnson company. Dermabond® (a registered trademark of Johnson & Johnson Company, New Brunswick, N.J., or more particularly, 2-octyl cyanoacrylate works as a very low viscosity liquid monomer, which, when applied to the skin over the wound, rapidly (i.e., within seconds to minutes) polymerizes and forms a stiff, transparent protective coating. The polymerization is initiated by moisture on the skin or nucleophilic (e.g., —OH and —NH2) groups on the surface of the skin. Thus the -CA groups become chemically attached or bound to the skin such that the resultant poly(2-octyl cyanoacrylate) coating, in fact, becomes a chemical part of the skin.

Indermil® tissue adhesive (N-butyl-2-cyanoacrylate) is another wound closure product similar to Dermabond®, but is available from Covidien Co., a Henkel company. Indermil® is a registered trademark of Henkel Corporation, Rocky Hill, Conn. Histoacryl® topical skin adhesive (N-butyl-2-cyanoacrylate) is also a skin adhesive available from B. Braun Corporation. Histoacryl® is a registered trademark of Aesculap, Inc., Center Valley, Pa. Both of these adhesives are based upon the N-butyl-2 cyanoacrylate which chemically differs from 2-octyl cyanoacrylate.

However, each of these contemporary cyanoacrylate-based products has its drawbacks. For instance, all of these products produce stiff films or coatings upon polymerizing shortly after application and, therefore, have the problem of sloughing off easily after application and drying, particularly when the skin is in motion. Thus Dermabond® and the other contemporary cyanoacrylate-based wound closures or adhesives cannot be applied where the skin is in frequent motion, i.e., over the elbow, knee, knuckles, wrist, face, etc. Application at these sites would require a flexible or rubbery wound cover. Furthermore, each of these products is not oxygen permeable or breathable and, therefore, is a barrier to oxygen necessary for healing of the skin. Still further, many of these contemporary cyanoacrylate-based wound closures and adhesives are occlusive, meaning they do not allow the evaporation of water vapor caused by exudates within the wound during the healing process. Again, this prevents or delays the healing of the wound.

Still other deficiencies of one or more of the contemporary cyanoacrylate-based wound closures or adhesives are the low viscosity of some of the liquid forms. For example, Dermabond® has a low viscosity and is therefore "runny". It is well known to travel uncontrollably and rapidly over surfaces and enters into cuts or wounds where it polymerizes. Because it cannot be completely controlled and polymerizes rapidly (within seconds or minutes), it becomes a stiff polymer over the wound. Because it is not breathable, it further delays healing of the wound. This may also be an issue should the product get under the skin. While the toxicity of Dermabond® is sufficiently low to be used on the surface of the skin, it is still inappropriate for under-the-skin use and cannot be used for subcutaneous applications such as, for example, for use as implantable anti-adhesive for organ coatings.

With respect to the problem of stiffness, attempts have heretofore been made to address this issue. Contemporary research has reduced to practice polyisobutylenes endowed with or functionalized with cyanoacrylate groups (PIB-CA), which provide significantly improved flexibility over the contemporary cyanoacrylate-based products mentioned hereinabove. Such cyanoacrylate-functionalized polyisobutylenes have been used to provide flexible transparent wound closures with good mechanical properties with respect to tensile strength and elongation. However, like the contemporary cyanoacrylate-based wound closures and adhesives above, these polyisobutylene-based wound closures are not breathable and are barriers to gases and vapors (moisture) so as to not allow for the evaporation of exudates within the wound. Thus, it is well known that polyisobutylene is used as flexible air-and-moisture impermeable skin adhesives and closures, for example, as a constituent in colostomy patches.

There are also a number of medical grade silicone adhesives on the market today. However, some of these silicone adhesives, such as SILASTIC® Medical Adhesive Silicone, Type A, are used to bond elastomers, synthetics and metals for part fabrication and medical devices. They are not used as wound closures or wound adhesives and do not contain cyanoacrylates. SILASTIC® Medical Adhesive Silicone, available from Dow Corning Corporation, is a one-part, low-slump, translucent silicone material that is solventless and cures at room temperature between 50-60% relative humidity. SILASTIC® is a registered trademark of Dow Corning Corporation, Midland, Mich. There are also silicone adhesive tapes available on the market today. An example of such a product is 3M™ Kind Removal Silicone Tape, available from 3M Corporation, St. Paul, Minn. Again, such silicone adhesive tapes also do not contain cyanoacrylates and are used to adhere various tubes and instruments to the skin, such as IVs and the like. They are not used as wound closures or wound adhesives.

Further, it should be understood that there are a line of products available on the market today that are called "silicone adhesives" or "silicone rubber adhesives" that are not made of silicone rubbers at all. Instead, these products are used to bond silicone rubber to other things such as metal, synthetic, or other rubber products. That is, they are named after that to which they adhere, not that of which what they are made.

There are, however, at least a few wound dressing products that contain silicone rubber or silicone rubber foams on account of silicone's biocompatibility, appropriate mechanical properties, rubbery nature (flexibility), oxygen and gaseous water (vapor) permeability, optical transparency, and good "feel" on the skin. However, none of these silicone rubber-based products contain cyanoacrylates. In fact, many of them use polyurethane foam dressings with silicone adhesives for securing the foam dressing to the skin. Thus, the silicone adhesives are used in conjunction with additional layers for providing therapy to the wound.

There are literally hundreds of wound closure products on the market. A closer examination, however, reveals that the active constituents of these products are only a few, and the products differ only in name, appearance, and shape (marketing strategies). Most of these products are above, and a more detailed description of these products may be found in the books "*Clinical Guide to Skin and Wound Care*" (7th edition) by A. T. Hess, Wolters Kluwer Pub., 2013, and "*Wound Care*" (4th edition) by C. Sussman and B. Bates-Jensen, Wolters Kluwer Pub, 2012.

Thus, a need exists for a flexible, transparent polymeric composition that can be used as a wound closure, adhesive, sealant or skin protectant. Such a composition desirably includes all of the benefits of a cyanoacrylate-based composition, including its instantaneous adhesion to skin and its protective coating properties, as well as all of the benefits of a silicone rubber-based composition, including its biocompatibility, appropriate mechanical properties, rubbery nature (i.e., flexibility), oxygen and gaseous water (vapor) permeability, optical transparency, and good "feel" on the skin.

SUMMARY OF THE INVENTION

Any one or more of the foregoing aspects of the present invention, together with the advantages thereof over known art relating to cyanoacrylate-functionalized silicone rubbers, particularly for wound closures and adhesives, and the methods of synthesis of the same, which will become apparent from the specification that follows, may be accomplished by the invention as hereinafter described and claimed.

The present invention provides a silicone rubber functionalized with at least one cyanoacrylate group. In one or more embodiments, the silicone rubber is polydimethylsiloxane (PDMS). In other embodiments, the silicone rubber can be a methylhydrosiloxane-dimethylsiloxane diblock copolymer, a methylhydrosiloxane homopolymer, or a methylhydrosiloxane-dimethylsiloxane random copolymer having a cyanoacrylate-based substituent replacing the hydrogen attached to the Si within the methylhydrosiloxane moiety.

In one or more embodiments, the at least one cyanoacrylate group is a —O—CO—C(CN)=CH2 group. In one or more of these embodiments, the at least one cyanoacrylate group may be directly attached at a terminus end of the silicone rubber. This is particularly true where the silicone rubber is polydimethylsiloxane. In other embodiments, the at least one cyanoacrylate group is directly attached to the interior backbone of the silicone rubber. This is particularly true where the cyanoacrylate group is attached to the methylhydrosiloxane-substituted moiety within the methylhydrosiloxane homopolymers, methylhydrosiloxane-dimethylsiloxane diblock copolymer or methylhydrosiloxane-dimethylsiloxane random copolymer.

In one or more embodiments, the silicone rubber is functionalized with at least two cyanoacrylate groups. In some embodiments, the cyanoacrylate groups are attached to both or all terminus ends of a silicone rubber. In other embodiments, the cyanoacrylate groups are attached to only the interior backbone of the silicone rubber. Still in other embodiments, one or more of the cyanoacrylate groups are attached to one or more of the terminus ends of the silicone rubber, while one or more other cyanoacrylate groups are attached to one or more places within the backbone of the silicone rubber.

In one or more embodiments, the silicone rubber has a spacer group between the silicone rubber and at least one of the cyanoacrylate groups. In one or more of these embodiments, the spacer group is attached to a terminus end of the silicone rubber and the cyanoacrylate group is attached to the spacer group. In other embodiments, the spacer group is attached to the interior backbone of the silicone rubber and the cyanoacrylate group is attached to the spacer group. In one or more of these embodiments, the spacer group is a polyalkyl block. In one or more other embodiments, the spacer group is a polyalkylene oxide block. Where the spacer group is a polyalkyl block or a polyalkylene oxide block, the spacer group may have from 1 to 16 carbon atoms. In one embodiment, the spacer group is an allylic block. In one or more embodiments, the spacer group and cyanoacrylate group provide for a —CH2-CH2-CH2-CA substituent attached to the silicone rubber.

Another aspect of the present invention provides a method for the preparation of a silicone rubber-containing polymer endowed with one or more functionalized cyanoacrylate groups, the method comprising reacting (A) a silicone rubber selected from the group consisting of (a) a polydimethylsiloxane terminated with at least one group selected from (1) a silane (—SiH), (2) a silanol (—SiOH), (3) a carbinol having the formula (i) —Si—(CH$_2$)$_z$OH where z is an integer 1 to 18, and (4) a carbinol having the formula (ii) —Si(CH$_2$)$_z$(OCH$_2$CH$_2$)$_m$OH wherein z is an integer 1 to 18 and m is an integer 1 to 16, (b) a methylhydrosiloxane-dimethylsiloxane diblock polymer, (c) a methylhydrosiloxane homopolymer, and (d) a methylhydrosiloxane-dimethylsiloxane random copolymer, with (B) a protected cyanoacrylate adduct selected from the group consisting of (1) an anthracene/2-cyanoacryloyl chloride adduct having the formula wherein the 2-cyanoacryloyl chloride is protected, and (2) an anthracene/alkenyl 2-cyanoacrylate adduct having the formula wherein k is an integer from 1 to 16 and wherein the alkenyl 2-cyanoacrylate is protected, with the proviso that the (B)(1) anthracene/2-cyanoacryloyl chloride adduct is used where one or more hydroxyl (—OH) termini are present in the silicone rubber and the (B)(2) anthracene/alkenyl 2-cyanoacrylate adduct is used where one or more silane (SiH) groups are present in the silicone rubber, wherein the reaction provides a silicone rubber endowed with at least one anthracene-protected 2-cyanoacrylate group selected from protected 2-cyanoacrylate and protected alkenyl 2-cyanoacrylate; and deprotecting the at least one anthracene-protected 2-cyanoacrylate group with maleic anhydride to form the silicone rubber-containing polymer endowed with one or more functionalized cyanoacrylate groups.

In one or more embodiments, the step of reacting includes esterificating (i.e., providing an esterification reaction) each terminus end of the polydimethylsiloxane terminated with a group selected from (a) a silanol (—SiOH), (b) a carbinol having the formula (i) —Si—(CH$_2$)$_z$OH where z is an integer 1 to 18, or a carbinol having the formula (ii) —Si(CH$_2$)$_z$(OCH$_2$CH$_2$)$_m$OH wherein z is an integer 1 to 18 and m is an integer 1 to 16, with the anthracene/2-cyanoacryloyl chloride adduct. In another embodiment, the step of reacting includes hydrosilating the anthracene/alkenyl 2-cyanoacrylate adduct with each terminus end of the polydimethylsiloxane terminated with a silane. In yet one or more other embodiments, the step of reacting includes hydrosilating the anthracene/alkenyl 2-cyanoacrylate adduct with at least one SiH group present in the silicone rubber selected from (b) the methylhydrosiloxane-dimethylsiloxane diblock polymer, (c) the methylhydrosiloxane homopolymer, and (d) the methylhydrosiloxane-dimethylsiloxane random copolymer.

In one or more embodiments, the step of deprotecting includes reacting the maleic anhydride with the at least one protected 2-cyanoacrylate, to form a 2-cyanoacrylate terminated polydimethylsiloxane. In other embodiments, the step of deprotecting includes reacting the maleic anhydride with the at least one protected alkenyl 2-cyanoacrylate endowed on the silicone rubber, to form 2-cyanoacrxyloxyalkyl-terminated polydimethylsiloxane where the silicone rubber was the polydimethylsiloxane terminated with a silane, polydimethylsiloxane-b-poly[(2-cyanoacryloxyalkyl) methylsiloxane)] where the silicone rubber was the methylhydrosiloxane-dimethylsiloxane diblock polymer, poly(2-cyanoacryloxyalkyl methylsiloxane) where the silicone rubber was the methylhydrosiloxane homopolymer, and poly[(2-cyanoacryloxyalkyl) methylsiloxane-co-dimethylsiloxane] where the silicone rubber was the methylhydrosiloxane-dimethylsiloxane random copolymer.

A further aspect of the present invention provides a silicone rubber selected from the group consisting of 2-cyanoacrylate-terminated polydimethylsiloxane, a block copolymer of polydimethylsiloxane and poly[2-cyanoacryloxyalkyl)methylsiloxane, a random copolymer of poly[(2-cyanoacryloxyalkyl) methylsiloxane and polydimethylsiloxane, a homopolymer of a poly(2-cyanoacryloxyalkyl methylsiloxane) and combinations and blends thereof. It will be appreciated that, where desired and because these silicone rubbers are chemically very similar, they form homogeneous blends. Such silicone rubbers are useful as wound care products such as a wound closure, a wound adhesive, a wound sealant or a skin protector.

Beneficially, it will be appreciated that, from the synthesis of these silicone rubbers, wound care products may be produced that can be readily attached to the skin and are oxygen and water vapor permeable. In some embodiments, it will be appreciated that the silicone rubbers employed, such as particularly PDMS, have high molecular weight and therefore, result in providing flexibility to the wound care product or wound closure. It will also be appreciated that some of the silicone rubbers, particularly the homopolymer, and diblock or random copolymers, can contain a large number of cyanoacrylate groups and, therefore, will increase the rate of curing (set time) required for the wound care product or wound closure. Thus, by selecting appropriate blend ratios of these groups of silicone rubbers the flexibility and curing time of the wound care product or wound closure can be fine-tuned to a desired flexibility or cure time.

DESCRIPTION OF ONE OR MORE DETAILED EMBODIMENTS

The present invention provides a family of polymeric materials that can be used as, inter alia, wound care products such as wound closures, wound adhesives, wound sealants, and skin protectors. The polymeric materials are silicone rubbers that are endowed with one or more cyanoacrylate groups so as to exhibit a combination of properties from both constituents, the silicone rubber moiety and the cyanoacrylate moiety.

The silicone rubber (SiR) moiety provides oxygen and moisture permeability, or breathability, not found is other contemporary materials currently used in the wound care industry. The silicone rubber moiety also provides several other desirable properties common to this unique rubber, such as good elasticity, good mechanical properties (e.g., tensile strength and elongation), biocompatibility with living tissues and optical transparency, to name a few.

The cyanoacrylate group provides instantaneous adhesion or attachment to living tissue (e.g., skin, internal tissues, organs, etc.) or other products having moisture present. In wound care applications, by depositing a silicone rubber endowed with cyanoacrylate groups (SiR-CA) over wounds or lacerations, the disrupted skin will be rapidly covered by a strongly adherent, optically transparent, flexible, oxygen and moisture permeable ("breathable") coating or film.

Such a rubbery coating can be used on wounds that contemporary wound care products, such as Dermabond®, cannot. For example, the present invention is envisioned as being useful for application to flexible joints such as knees, knuckles, elbows, etc. where other contemporary wound closure products would slough off or crack due to a lack of flexibility upon polymerization and formation of the coating. Moreover, because the cyanoacrylate groups are attached to the silicone rubber, the resultant product is less viscous (i.e., has a higher viscosity) than contemporary cyanoacrylate-based wound care products themselves. Wound care products made from the present invention would also promote wound healing by protecting the skin and because the silicone rubber is breathable, i.e., permeable to gases such as water vapor and oxygen. Such breathability also allows for the evaporation of water vapor (exudates) and the like, which also promotes healing of the wound. Cyanoacrylate-based products, or products made from polyisobutylene with cyanoacrylate functionality, do not provide for such breathability.

The present invention provides for several convenient synthesis routes for introducing cyanoacrylate groups into silicone rubbers. Among these synthesis routes include (a) the esterification of (1) a silanol (e.g., PDMS containing SiOH groups) or (2) a carbinol-functional silicone rubber (e.g., PDMS containing —CH$_2$OH groups) by use of a protected 2-cyanoacryloyl halide, or (b) hydrosilation of protected alkenyl 2-cyanoacrylates with hydride functionalized silicone rubbers (i.e., polysiloxanes containing an SiH group), followed by deprotection of the cyanoacrylate group. Since cyanoacrylates react extremely rapidly with even traces of moisture (and nucleophiles in general), they are usually chemically protected from moisture. This may be accomplished by the use of a "protected" cyanoacrylate group, i.e., cyanoacrylates endowed with a protecting group. Preferably, the protecting group should be easy to remove after completing the desired reaction. Among well-known protecting groups for cyanoacrylate, anthracene is probably the most common. Essentially any protecting group that can be removed upon completion of the desired reaction would be suitable for this synthesis, although the easier the removal of the protecting group, the better and more economical the synthesis will be. It is well known that anthracene can be readily and easily removed from cyanoacrylates after reaction by heating with maleic anhydride. Thus, using an anthracene-protected 2-cyanoacryloyl halide in an esterification reaction or an anthracene-protected alkenyl 2-cyanoacrylate in a hydrosilation reaction as above will protect the 2-cyanoacryloyl halide or the alkenyl 2-cyanoacrylate from reacting during these reaction processes. The 2-cyanoacrylate group may then be deprotected by reaction with maleic anhydride, wherein the anthracene is removed and forms an anthracene/maleic anhydride adduct, while the 2-cyanoacrylate group is attached to the silicone rubber or polysiloxane.

As a result, several novel compositions have been developed. These compositions are all silicone rubber-based, and include either a polydialkylsiloxane or a polyalkylhydrosiloxane wherein any hydrogen attached directly to the Si (i.e., any silane (SiH) group) has been substituted for a cyanoacrylate group so as to form a polyalkyl(cyanoacrylate) siloxane. Where polydialkylsiloxane is used by itself, the polymer is terminated with the cyanoacrylate group at one or more of its terminus ends. Where the polyalkylhydrosiloxane is used, the cyanoacrylate group is attached to the interior backbone of the polyalkylsiloxane moiety. Thus, novel compositions include 2-cyanoacrylate-terminated polydimethylsiloxane, a block copolymer of polydimethylsiloxane and poly[2-cyanoacryloxyalkyl)methylsiloxane, a random copolymer of poly[(2-cyanoacryloxyalkyl) methylsiloxane and polydimethylsiloxane, a homopolymer of a poly(2-cyanoacryloxyalkyl methylsiloxane) and combinations and blends thereof.

In order to understand the various syntheses of the compositions, it will be appreciated that various Schemes have been set forth hereinbelow to provide a better understanding and a more detailed description of the embodiments of a suitable reaction scheme for the present invention. It will be appreciated that the reactions in the presented Schemes all use polydimethylsiloxanes (PDMSs) and/or polymethylhydrosiloxanes in the reaction schemes. However, it will be understood that other polydialkylsiloxanes or other polyalkylhydrosiloxanes can be used. Furthermore, if the polydialkylsiloxane has only one Si—OH group, the product will carry only one cyanoacrylate terminus. On the other hand, if the polydialkylsiloxane has several Si—OH groups distributed in the chain, several cyanoacrylate substituents will be introduced. Still further, it will be appreciated that the properties of the products can be fine-tuned by controlling the molecular weight of the silicone rubber (SiR) starting material. For cyanoacrylate-terminated PDMS effected by an esterification reaction and deprotection as set forth in Scheme 1, a molecular weight preferably greater than 400 g/mol is desired. More particularly, a (mole average) molecular weight range of between 4,600 g/mol and 150,000 g/mol can be employed. Still further a molecular weight range of between 4,600 g/mol and 60,000 g/mol is desired. Thus, in Scheme 1, n is at least 3, more preferably, an integer of from 60 to 2025 and, desirably an integer of from 60 to 810.

Scheme 1 below outlines the synthesis route for obtaining 2-cyanoacrylate-terminated polydimethylsiloxane (PDMS) by esterification and deprotection. More particularly, this esterification reaction can be effected by the use (i.e., cyanoacrylation) of silanols (i.e., any silicone rubber having terminal Si—OH groups), and as shown in Scheme 1, di-silanols, with the anthracene adduct of 2-cyanoacryloyl chloride. The esterification reaction results in the formation of a protected-2-cyanoacrylate-terminated PDMS, which can then be deprotected by reacting it with maleic anhydride. The deprotection reaction removes the anthracene from the cyanoacrylate, by forming an anthracene/maleic anhydride adduct, and resulting in the formation of 2-cyanoacrylate-terminated PDMS.

Scheme 1

2-Cyanoacrylate Terminated Polydimethylsiloxane

In order to demonstrate practice of this synthesis, the method for synthesizing 2-cyanoacrylate-terminated PDMS is carried out by first dissolving 20 g (0.068 mole) of anthracene/2-cyanoacryloyl chloride adduct in 40 mL of anhydrous methylene chloride in a 250 mL two-neck round bottom flask equipped with a magnetic stirrer, a dropping funnel and nitrogen inlet. A solution of 23.44 g silanol-terminated PDMS (0.068 mole OH-group, Gelest DMS-S12) and 10.32 g (0.102 mole) triethylamine in 40 mL dry methylene chloride are then added dropwise over about 30 minutes to the system at about 25-30° C. The reaction results in the formation of anthracene-protected 2-cyanoacrylate PDMS.

The deprotection step is carried out as described above and by a procedure similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. The system is refluxed at 140° C. for about 8 hours in the presence of maleic anhydride, where upon the anthracene/maleic anhydride adduct is suction filtered and the solvent is evaporated by distillation. The result 2-cyanoacrylate-terminated PDMS product is recovered as a colorless viscous liquid.

Scheme 2 below also outlines the synthesis route for obtaining 2-cyanoacrylate-terminated polydimethylsiloxane (PDMS) by esterification and deprotection, but this time relies on the cyanoacrylation of carbinol (hydroxyl) terminated PDMS with the anthracene adduct of 2-cyanoacryloyl chloride. More particularly, this esterification reaction can be effected by the use (i.e., cyanoacrylation) of carbinols (i.e., any silicone rubber having terminal —(CH$_2$)$_z$—OH groups, wherein z=1 to 18), and as shown in Scheme 2, di-carbinols, with the anthracene adduct of 2-cyanoacryloyl chloride. The esterification reaction results in the formation of a protected-2-cyanoacrylate-terminated PDMS, which can then be deprotected by reacting it with maleic anhydride. The deprotection reaction removes the anthracene from the cyanoacrylate, by forming an anthracene/maleic anhydride adduct, and resulting in the formation of 2-cyanoacrylate-terminated PDMS.

It will again be understood that other polydialkylsiloxanes can be used. Furthermore, if the polydialkylsiloxane has only one —(CH$_2$)$_z$—OH group, the product will carry only one cyanoacrylate terminus. On the other hand, if the polydialkylsiloxane has several —(CH$_2$)$_z$—OH groups distributed or grafted in the chain, several cyanoacrylate substituents will be introduced. Still further, it will be appreciated that the properties of the products can be fine-tuned by controlling the molecular weight of the silicone rubber (SiR) starting material. A higher molecular weight preferably greater than 500 g/mol is desired. More particularly, a (mole average) molecular weight range of between 600 g/mol and 100,000 g/mol can be employed. Still further a molecular weight range of between 4,600 g/mol and 60,000 g/mol is desired. Thus, in Scheme 2, n is at least 3, more preferably, an integer of from 4 to 1350 and, desirably an integer of from 58 to 810.

Scheme 2

2-Cyanoacrylate Terminated Polydimethylsiloxane

In order to demonstrate practice of this synthesis, the method for synthesizing 2-cyanoacrylate-terminated PDMS is carried out by first dissolving 20 g (0.068 mole) of anthracene/2-cyanoacryloyl chloride adduct in 40 mL of anhydrous methylene chloride in a 250 mL two-neck round bottom flask equipped with a magnetic stirrer, a dropping funnel and nitrogen inlet. A solution of 24.65 g carbinol (hydroxyl)-terminated PDMS (0.068 mole OH-group, Gelest DMS-S12) and 10.32 g (0.102 mole) triethylamine in 45 mL dry methylene chloride are then added dropwise over about 30 minutes to the system at about 25-30° C. The reaction results in the formation of anthracene-protected 2-cyanoacrylate PDMS.

The deprotection step is carried out as described above and by a procedure similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. The system is refluxed at 140° C. for about 8 hours in the presence of maleic anhydride, where upon the anthracene/maleic anhydride adduct is suction filtered and the solvent is evaporated by distillation. The result 2-cyanoacrylate-terminated PDMS product is recovered as a colorless viscous liquid.

Scheme 3 below outlines yet a third synthesis route for obtaining 2-cyanoacrylate-terminated polydimethylsiloxane (PDMS) by esterification and deprotection, but this time relies on the cyanoacrylation of a larger carbinol (hydroxyl) terminated PDMS with the anthracene adduct of 2-cyanoacryloyl chloride. More particularly, this esterification reaction can be effected by the use (i.e., cyanoacrylation) of a second group of carbinols (i.e., any silicone rubber having terminal —$(CH_2)_z$—$(OCH_2CH_2)_m$—OH groups, wherein z=1 to 18 and m=1 to 16), and as shown in Scheme 3, di-carbinols, with the anthracene adduct of 2-cyanoacryloyl chloride. The esterification reaction results in the formation of a protected-2-cyanoacrylate-terminated PDMS, which can then be deprotected by reacting it with maleic anhydride. The deprotection reaction removes the anthracene from the cyanoacrylate, by forming an anthracene/maleic anhydride adduct, and resulting in the formation of 2-cyanoacrylate-terminated PDMS.

It will again be understood that other polydialkylsiloxanes can be used. Furthermore, if the polydialkylsiloxane has only one —$(CH_2)_z$—$(OCH_2CH_2)_m$—OH group, the product will carry only one cyanoacrylate terminus. On the other hand, if the polydialkylsiloxane has several —$(CH_2)_z$—$(OCH_2CH_2)_m$—OH groups distributed or grafted in the chain, several cyanoacrylate substituents will be introduced. Still further, it will be appreciated that the properties of the products can be fine-tuned by controlling the molecular weight of the silicone rubber (SiR) starting material. A higher molecular weight preferably greater than 500 g/mol is desired. More particularly, a (mole average) molecular weight range of between 600 g/mol and 100,000 g/mol can be employed. Still further a molecular weight range of between 4,600 g/mol and 60,000 g/mol is desired. Thus, in Scheme 3, n is at least 2, more preferably, an integer of from 3 to 1350 and, desirably an integer of from 57 to 810.

In order to demonstrate practice of this synthesis, the method for synthesizing 2-cyanoacrylate-terminated PDMS is carried out by first dissolving 20 g (0.068 mole) of anthracene/2-cyanoacryloyl chloride adduct in 40 mL of anhydrous methylene chloride in a 250 mL two-neck round bottom flask equipped with a magnetic stirrer, a dropping funnel and nitrogen inlet. A solution of 34.05 g carbinol (hydroxyl)-terminated PDMS (0.068 mole OH-group, Gelest DMS-S15, z=3, m=1, 1000 g/mol) and 10.32 g (0.102 mole) triethylamine in 45 mL dry methylene chloride are then added dropwise over about 30 minutes to the system at about 25-30° C. The reaction results in the formation of anthracene-protected 2-cyanoacrylate PDMS.

The deprotection step is carried out as described above and by a procedure similar to that in the literature. (*Unequivocal Synthesis of Bis*(2-*Cyanoacrylate*) *Monomers. I. Via Anthracene Adducts*, J. Polym. Sci.: Polym. Chem. Ed., Vol. 16, 2475-2507 (1978)), the disclosure of which is incorporated herein by reference. The solution of anthracene-protected 2-cyanoacrylate PDMS in xylene is refluxed at 140° C. for about 8 hours in the presence of maleic anhydride, where upon the anthracene/maleic anhydride adduct is suction filtered and the solvent is evaporated by distillation. The result 2-cyanoacrylate-terminated PDMS product is recovered as a colorless viscous liquid.

Scheme 4 below outlines a synthesis route for obtaining 2-cyanoacrylate-terminated polydimethylsiloxane (PDMS) by hydrosilation and deprotection, but this time relies on the hydrosilation of the adduct of anthracene/alkenyl 2-cyanoacrylates with PDMS containing silane (SiH) groups. More particularly, this hydrosilation reaction can be effected by the use of the anthracene/alkenyl 2-cyanoacryloyl chloride adduct that protects the 2-cyanoacrylate group from moisture with a hydride-terminated PDMS (i.e., any silicone rubber having a terminal SiH group), and as shown in Scheme 4, di-hydride groups. The alkenyl (vinyl) group may be of any length desired, but typically will include from 1 to 16 $CH_2$ groups attached to the double bonded carbon. The hydrosilation reaction is well known and uses a Karstedt catalyst to force the reaction of the alkenyl group and the silane (SiH) group, so at to provide a resulting product of a protected-2-cyanoacrylate-terminated PDMS, which can then be deprotected by reacting it with maleic anhydride. The deprotection reaction removes the anthracene from the cyanoacrylate, by forming an anthracene/maleic anhydride adduct, and resulting in the formation of an unprotected 2-cyanoacrylate-terminated PDMS.

It will again be understood that other polydialkylsiloxanes can be used, but that at least one terminus of the polyalkylsiloxane must contain a SiH group. Furthermore, if the polydialkylsiloxane has only one SiH group, the product will carry only one cyanoacrylate terminus. On the other hand, if the polydialkylsiloxane has several SiH groups distributed in the chain, several cyanoacrylate substituents will be introduced. Still further, it will be appreciated that the properties of the products can be fine-tuned by controlling the molecular weight of the silicone rubber (SiR) starting material. A higher molecular weight preferably greater than 400 g/mol is desired. More particularly, a (mole average) molecular weight range of between 500 g/mol and 100,000 g/mol can be employed. Still further a molecular weight range of between 17,000 g/mol and 62,000 g/mol is desired. Thus, in Scheme 4, n is at least 3, more preferably, an integer of from 4 to 1350 and, desirably an integer of from 227 to 840.

Scheme 4

In order to demonstrate practice of this synthesis, the method for synthesizing 2-cyanoacrylate-terminated PDMS is carried out by first placing 5 g (9 mmole SiH group, Gelest DMS-H11, 1100 g/mol) SiH-terminated PDMS in a 100 mL Schlenk flask sealed with a rubber septum and equipped with a magnetic stirrer and nitrogen inlet. 2.84 g (9 mmole anthracene/allyl 2-cyanoacrylate adduct (k=1) is added to the flask and the contents are dissolved in about 15 mL anhydrous methylene chloride. The ratio of SiH groups to vinyl groups is desirably 1:1. After the addition of the Karstedt catalyst, which in this case was platinum-divinyltetramethyl-disiloxane complex in xylene, 2.1-2.4% Pt, (Gelest SIP6831.2), the solution is stirred at room temperature for about 24 hours. The solvent is then removed by a rotary evaporator, and the crude (grey) product dissolved in 200 mL hexane. The hexane solution is passed through alumina (activated neutral) column to remove the catalyst and other impurities. The completion of the hydrosilation and the structure of the product are determined by $^1$H NMR spectroscopy.

The deprotection step is carried out as described above and by a procedure similar to that in the literature. (*Unequivocal Synthesis of Bis*(2-*Cyanoacrylate*) *Monomers. I. Via Anthracene Adducts*, J. Polym. Sci.: Polym. Chem. Ed., Vol. 16, 2475-2507 (1978)), the disclosure of which is incorporated herein by reference. The system is refluxed at 140° C. for about 8 hours in the presence of maleic anhydride, where upon the anthracene/maleic anhydride adduct is suction filtered and the solvent is evaporated by a rotary evaporator. The result 2-cyanoacrylate-terminated PDMS product is recovered as a colorless viscous liquid.

Scheme 5 below outlines a synthesis route for obtaining a block copolymer of PDMS and poly[(2-cyanoacryloxyalkyl)methylsiloxane] (herein also described as "PDMS-b-poly[(2-cyanoacryloxyalkyl)methylsiloxane]") by hydrosilation and deprotection, as well as a synthesis route for obtaining poly(2-cyanoacryloxyalkyl methylsiloxane) by hydrosilation and deprotection. Both hydrosilation reactions employ the adduct of anthracene/alkenyl 2-cyanoacrylates with either a methylhydrosiloxane-dimethylsiloxane diblock copolymer or a methylhydrosiloxane homopolymer, respectively. More particularly, this hydrosilation reaction can be effected by the use of the anthracene/alkenyl 2-cyanoacrylate adduct that protects the 2-cyanoacrylate group from moisture with either of the above siloxane diblock polymer or siloxane homopolymer. In either case, the alkenyl (vinyl) group may be of any length desired, but typically will include from 1 to 16 $CH_2$ groups attached to the double bonded carbon.

As shown in Scheme 5, the methylhydrosiloxane-dimethylsiloxane diblock copolymer is provided. The number of units, n, in the PDMS block may be from 0 to 1700, while the number of units, m, in the polymethylhydrosiloxane may be from 1 to 1700. It will be appreciated that, where n=0, the composition used is a polymethylhydrosiloxane homopolymer.

As above for Scheme 4, the hydrosilation reaction is well known and uses a Karstedt catalyst to force the reaction of the alkenyl (vinyl) group and the silane (SiH) groups within the polymethylhydrosiloxane block, so at to provide a resulting product of a PDMS-b-poly[(anthracene protected 2-cyanoacryloxyalkyl) methylsiloxane, which can then be deprotected by reacting it with maleic anhydride. In Scheme 5, the alkenyl group is an allyl (k=1). The deprotection reaction removes the anthracene from the cyanoacrylate, by forming an anthracene/maleic anhydride adduct, and resulting in the formation of an unprotected PDMS-b-poly[(2-cyanoacryloxyalkyl)methylsiloxane, or where n=0, an unprotected poly(2-cyanoacryloxyalkylmethylsiloxane).

It will be understood that other polydialkylsiloxanes can be used and other polyalkylhydrosiloxanes can be used in this invention. The alkyl group is only limited by the issue of steric hindrance. However, it is required that at least one SiH group be present in order for the hydrosilation reaction to occur. Thus, it will be appreciated that each SiH group set forth in the polyalkylhydrosiloxane will react with the alkenyl (vinyl) group in the adduct of anthracene/alkenyl 2-cyanoacrylates. Thus, if only one SiH group exists (m=1), but the product will carry only one cyanoacrylate group. On the other hand, if the polydialkylhydrosiloxane has several SiH groups distributed in the chain, several cyanoacrylate substituents will be introduced. Still further, it will be appreciated that the properties of the products can be fine-tuned by controlling the molecular weight of the silicone rubber (SiR) starting material. A higher molecular weight preferably greater than 500 g/mol is desired. More particularly, a (mole average) molecular weight range of between 900 g/mol and 100,000 g/mol can be employed. Still further a molecular weight range of between 20,000 g/mol and 60,000 g/mol is desired. Thus, in Scheme 5, m is at least 1, more preferably, an integer of from 1 to 1660 and, desirably an integer of from 330 to 1000. In Scheme 5, n can be 0 and is preferably an integer ranging from 1 to 1660 and desirably from 330 to 1000.

Scheme 5

Methylhydrosiloxane-Dimethylsiloxane
Diblock Polymers or Methylhydrosiloxane
HomoPolmer (n=0)

Anthracene/Alkenyl 2-Cyanoacrylate
Adduct (protected-CA) k = 1-16

Karstedt catalyst

PDMS-b-Poly[(2-Cyanoacryloxyalkyl)Methylsiloxane] or
Poly(2-Cyanoacryloxyalkyl Methylsiloxane), where n=0

In order to demonstrate practice of this synthesis, the method for synthesizing PDMS-b-poly[(2-cyanoacryloxyalkyl)methylsiloxane], is carried out by first placing 5 g (20.4 mmole SiH group) poly(methylhydrosiloxane-b-dimethylsiloxane) in a 100 mL Schlenk flask sealed with a rubber septum and equipped with a magnetic stirrer and nitrogen inlet. 6.43 g (20.4 mmole anthracene/allyl 2-cyanoacrylate adduct (k=1) is added to the flask and the contents are dissolved in about 25 mL anhydrous tetrahydrofuran (THF). The ratio of SiH groups to vinyl groups is desirably 1:1. After the addition of the Karstedt catalyst, which in this case was platinum-divinyltetramethyl-disiloxane complex in xylene, 2.1-2.4% Pt, (Gelest SIP6831.2), the solution is stirred at room temperature for about 24 hours. The solvent is then removed by a rotary evaporator, and the crude (grey) product dissolved in 200 mL hexane. The hexane solution is passed through alumina (activated neutral) column to remove the catalyst and other impurities. The completion of the hydrosilation and the structure of the product are determined by $^1$H NMR spectroscopy.

The deprotection step is carried out as described above and by a procedure similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. The system is refluxed at 140° C. for about 8 hours in the presence of maleic anhydride, where upon the anthracene/maleic anhydride adduct is suction filtered and the solvent is evaporated by a rotary evaporator. The result 2-cyanoacrylate-terminated PDMS product is recovered as a colorless viscous liquid.

In order to demonstrate practice of this synthesis, the method for synthesizing poly(2-cyanoaryloxyalkyl methylsiloxane) (where n=0), is carried out by first placing 5 g (76.9 mmole SiH group) polymethylhydrosiloxane in a 100 mL Schlenk flask sealed with a rubber septum and equipped with a magnetic stirrer and nitrogen inlet. 26.68 g (84.6 mmole anthracene/allyl 2-cyanoacrylate adduct (k=1) is added to the flask and the contents are dissolved in about 20 mL anhydrous toluene. The ratio of SiH groups to vinyl groups is desirably 1:1.1. After the addition of the Karstedt catalyst, which in this case was platinum-divinyltetramethyl-disiloxane complex in xylene, 2.1-2.4% Pt, (Gelest SIP6831.2), the solution is stirred at room temperature for about 24 hours. The solvent is then removed by a rotary evaporator, and the crude (grey) product dissolved in 200 mL hexane. The hexane solution is passed through alumina (activated neutral) column to remove the catalyst and other impurities. The completion of the hydrosilation and the structure of the product are determined by $^1$H NMR spectroscopy.

The deprotection step is carried out as described above and by a procedure similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. The solution of anthracene-protected 2-cyanoacrylate PDMS in xylene is refluxed at 140° C. for about 8 hours in the presence of maleic anhydride, where upon the anthracene/maleic anhydride adduct is suction filtered and the solvent is evaporated by distillation. The result 2-cyanoacrylate-terminated PDMS product is recovered as a colorless viscous liquid.

Scheme 6 below outlines a synthesis route for obtaining a random copolymer of PDMS and poly[(2-cyanoacryloxyalkyl)methylsiloxane] (herein also described as "poly[(2-cyanoacryloxyalkyl)methylsiloxane-co-dimethylsiloxane]") by hydrosilation and deprotection. Like scheme 5, this hydrosilation reaction employs the adduct of anthracene/alkenyl 2-cyanoacrylate with a methylhydrosiloxane-dimethylsiloxane random copolymer. More particularly, this hydrosilation reaction can be effected by the use of the anthracene/alkenyl 2-cyanoacrylate adduct that protects the 2-cyanoacrylate group from moisture with the above siloxane random polymer. The alkenyl (vinyl) group may be of any length desired, but typically will include from 1 to 16 $CH_2$ groups attached to the double bonded carbon.

As shown in Scheme 6, the methylhydrosiloxane-dimethylsiloxane random copolymer is provided. The number of units, y, of dimethylsiloxane may be from 1 to 1700, while the number of units, x, in the methylhydrosiloxane may be from 1 to 1700.

As above for Schemes 4 and 5, the hydrosilation reaction is well known and uses a Karstedt catalyst to force the reaction of the alkenyl (vinyl) group and the silane (SiH) groups within the methylhydrosiloxane, so at to provide a resulting product of a poly[(anthracene protected 2-cyanoacryloxyalkyl) methylsiloxane-co-dimethylsiloxane], which can then be deprotected by reacting it with maleic anhydride. In Scheme 6, the alkenyl group is an allyl (k=1). The deprotection reaction removes the anthracene from the cyanoacrylate, by forming an anthracene/maleic anhydride adduct, and resulting in the formation of an unprotected poly[(2-cyanoacryloxyalkyl)methylsiloxane-co-dimethylsiloxane].

It will be understood that other polydialkylsiloxanes can be used and other polyalkylhydrosiloxanes can be used in this invention. The alkyl group is only limited by the issue of steric hindrance. However, it is required that at least one SiH group be present in order for the hydrosilation reaction to occur. Thus, it will be appreciated that each SiH group set forth in the polyalkylhydrosiloxane will react with the alkenyl (vinyl) group in the adduct of anthracene/alkenyl 2-cyanoacrylates. Thus, if only one SiH group exists (x=1), the product will carry only one cyanoacrylate group. On the other hand, if the polydialkylhydrosiloxane has several SiH groups distributed in the chain, several cyanoacrylate substituents will be introduced. Still further, it will be appreciated that the properties of the products can be fine-tuned by controlling the molecular weight of the silicone rubber (SiR) starting material. A higher molecular weight preferably greater than 500 g/mol is desired. More particularly, a (mole average) molecular weight range of between 1,000 g/mol and 100,000 g/mol can be employed. Still further a molecular weight range of between 20,000 g/mol and 60,000 g/mol is desired. Thus, in Scheme 5, x is at least 10, more preferably, an integer of from 13 to 1660 and, desirably an integer of from 240 to 1100. In Scheme 6, y can be 0 and is preferably an integer ranging from 0 to 1660.

Scheme 6

Figure 1:
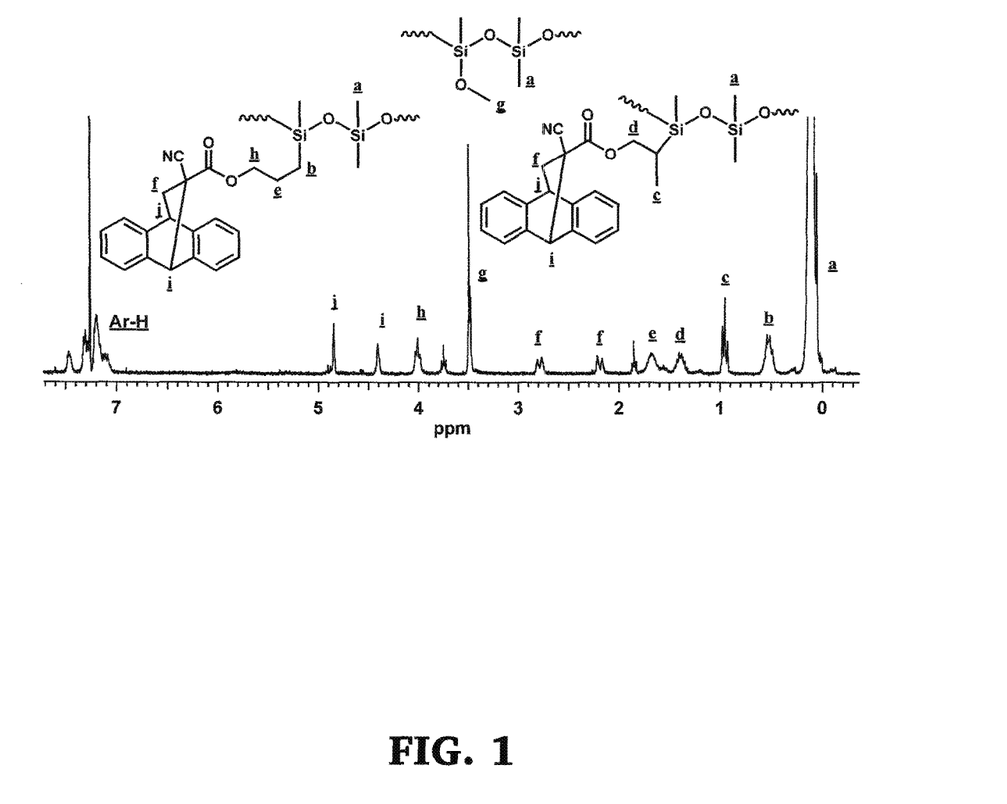
FIG. 1 is an NMR spectrum of an poly[(anthracene protected 2-cyanoacryloxyalkyl) methylsiloxane-dimethylsiloxane] random copolymer in accordance with the present invention with the appropriate assignments provided.

In order to demonstrate practice of this synthesis, the method for synthesizing poly[(2-cyanoacryloxyalkyl)methylsiloxane-co-dimethylsiloxane] was carried out by first placing 5 g (0.02 mmole SiH group) methylhydrosiloxane-dimethylsiloxane copolymer (Gelest HMS-301, 1900-2000 g/mol) in a 50 mL round bottom flask equipped with a magnetic stirrer and charged under a blanket of nitrogen at about 25-30° C. 7.08 g (0.023 mmole) anthracene protected allyl 2-cyanoacrylate adduct (k=1) dissolved in 20 mL anhydrous THF is added to the flask. The ratio of SiH groups to vinyl groups is desirably about 1:1. Next, after adding about 200 µL of Karstedt catalyst, which in this case was platinum-divinyltetramethyl-disiloxane complex in xylene, 2.1-2.4% Pt, Gelest SIP6831.2), reaction occurred. The solution was stirred at room temperature for about 5 hours, precipitated into a methanol/water mixture (250 mL/40 mL) at 0° C., and after about 2 hours, decanted. A yellow viscous (honey-like) substance was obtained. The completion of the hydrosilation and the structure of the product were determined by $^1$H NMR spectroscopy as shown in FIG. 1, together with assignments. Conversion of SiH via hydrosilation was about 29%, with provided about 2.3 g of the desired poly[(anthracene protected 2-cyanoacryloxyalkyl) methylsiloxane-dimethylsiloxane] random copolymer. The yield was 83%.

Figure 2:
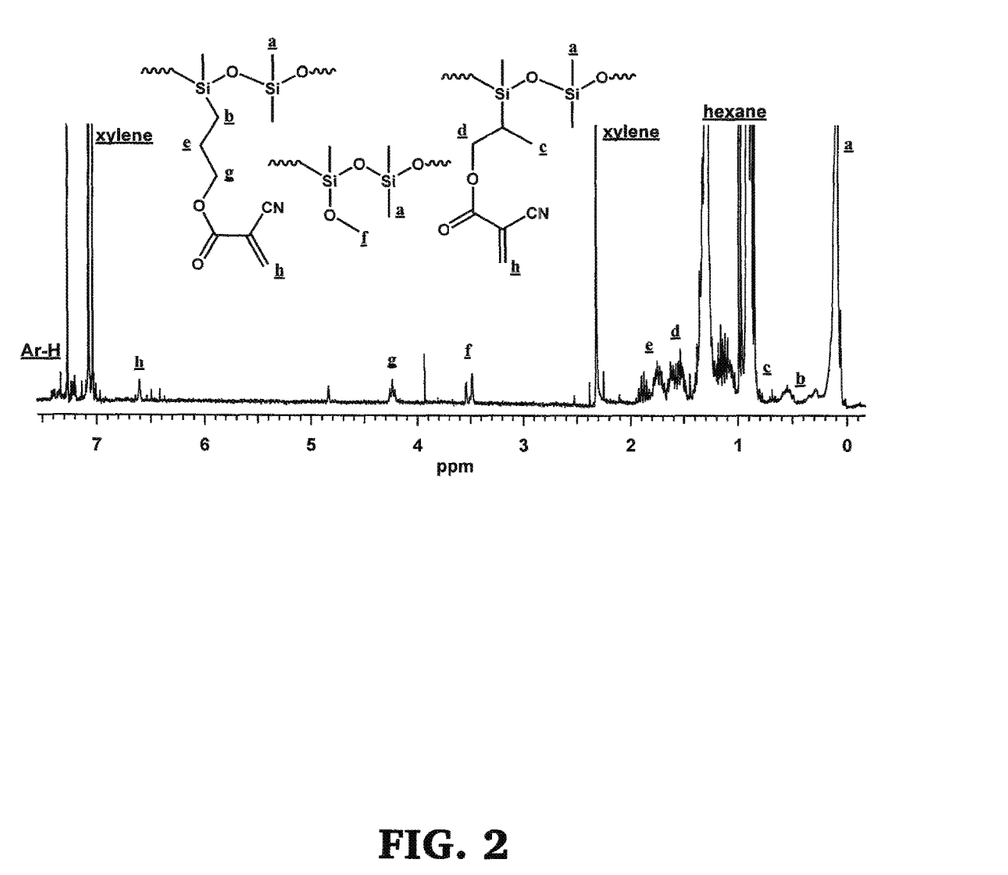
FIG. 2 is an NMR spectrum of a poly[(2-cyanoacryloxyalkyl) methylsiloxane-dimethylsiloxane] random copolymer according to the present invention with the appropriate assignments provided.

The deprotection step is carried out as described above, by the retro Diels-Alder reaction. This procedure is similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. More particularly, 5.68 g (8.53 mmole of anthracene/allyl cyanoacrylate groups) of the poly[(anthracene protected 2-cyanoacryloxyalkyl) methylsiloxane-dimethylsiloxane] was dissolved in 20 mL of freshly distilled xylene in a well dried 250 mL three neck round bottom flask equipped with a condenser and a magnetic stirrer. $SO_2$ inhibitor was bubbled into it for 30 minutes. The flask included 1.67 g (17.06 mmole) pulverized maleic anhydride and 74.9 mg $P_2O_5$. The mixture was stirred at reflux (about 140° C.) for about 8 hours, wherein the xylene was then distilled off. The remaining crude product was dissolved in 30 mL dry hexane. The anthracene/maleic anhydride adduct was then filtered and hexane was removed by distillation. The product, poly [(2-cyanoacryloxyalkyl) methylsiloxane-co-dimethylsiloxane], was a light yellow greasy liquid. Conversion of the protected allyl cyanoacrylate to the allyl cyanoacrylate groups was 92%, equivalent to 2.1 g/mol poly[(2-cyanoacryloxyalkyl) methylsiloxane-co-dimethylsiloxane]. The yield was 96%. FIG. 2 shows the NMR spectrum of the product with assignments.

In a second sample, a higher (20-25,000 g/mol) molecular weight product was provided. The method for synthesizing poly[(2-cyanoacryloxyalkyl) methylsiloxane-co-dimethylsiloxane] was carried out by first placing 16.38 g (0.011 mole SiH group) methylhydrosiloxane-dimethylsiloxane copolymer (Gelest HMS-053, 20,000-25,000 g/mol) in a 100 mL round bottom flask equipped with a magnetic stirrer and charged under a blanket of nitrogen at about 25-30° C. 3.82 g (0.012 mole) anthracene protected allyl 2-cyanoacrylate adduct (k=1) was dissolved in 20 mL anhydrous toluene and another 10 mL of anhydrous toluene was added to the flask. The ratio of SiH groups to vinyl groups was about 1:1. The mixture was cooled to −5° C. and about 50 µL of Karstedt catalyst, (again, platinum-divinyltetramethyl-disiloxane complex in xylene, 2.1-2.4% Pt, Gelest SIP6831.2) was added. Again, reaction occurred. The solution was stirred at room temperature for about 24 hours, precipitated into methanol (450 mL) at 0° C., and after about 1 hour, the methanol was decanted. A honey-like, colorless product was obtained. This product was dissolved in hexane (150 mL) and washed three times with distilled water (50 mL). The solution was dried over $MgSO_4$ overnight. The $MgSO_4$ was filtered off, and the hexane was removed by a rotary evaporator. The completion of the hydrosilation and the structure of the product were determined by $^1$H NMR spectroscopy. Conversion of SiH via hydrosilation was about 58%, with provided about 8-10 g/mol of the desired poly[(anthracene protected 2-cyanoacryloxyalkyl) methylsiloxane-dimethylsiloxane] random copolymer. The yield was 68%.

The deprotection step is carried out as described above, by the retro Diels-Alder reaction. This procedure is similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. More particularly, 13.67 g (5.48 mmole of anthracene/allyl cyanoacrylate groups) of the poly[(anthracene protected 2-cyanoacryloxyalkyl) methylsiloxane-dimethylsiloxane] was dissolved in 50 mL of freshly distilled xylene in a well dried 250 mL three neck round bottom flask equipped with a condenser and a magnetic stirrer. $SO_2$ inhibitor was bubbled into it for 30 minutes. The flask included 1.07 g (10.9 mmole) pulverized maleic anhydride and 57.5 mg $P_2O_5$. The mixture was stirred at reflux (about 140° C.) for about 8 hours, wherein the xylene was then distilled off. The remaining crude product was dissolved in 40 mL dry hexane. The anthracene/maleic anhydride adduct was then filtered and hexane was removed by distillation. The product, poly [(2-cyanoacryloxyalkyl) methylsiloxane-co-dimethylsiloxane], was a colorless greasy liquid. Conversion of the protected allyl cyanoacrylate to the allyl cyanoacrylate groups was 92%, equivalent to 7.8-9.5 poly[(2-cyanoacryloxyalkyl) methylsiloxane-co-dimethylsiloxane]. The yield was 95%.

In a third sample, an even higher molecular weight (50-60,000 g/mol) product was provided. The method for synthesizing poly[(2-cyanoacryloxyalkyl) methylsiloxane-co-dimethylsiloxane] was carried out by first placing 15.05 g (0.013 mole SiH group) methylhydrosiloxane-dimethylsiloxane copolymer (Gelest HMS-064, 50,000-60,000 g/mol) in a 100 mL round bottom flask equipped with a magnetic stirrer and charged under a blanket of nitrogen at about 25-30° C. 4.2 g (0.013 mole) anthracene protected allyl 2-cyanoacrylate adduct (k=1) was dissolved in 10 mL anhydrous toluene and another 40 mL of anhydrous toluene was added to the flask. The ratio of SiH groups to vinyl groups was about 1:1. The mixture was cooled to −5° C. and about 100 µL of Karstedt catalyst, (again, platinum-divinyltetramethyl-disiloxane complex in xylene, 2.1-2.4% Pt, Gelest SIP6831.2) was added. Again, reaction occurred. The solution was stirred at room temperature for about 24 hours, precipitated into methanol (500 mL) at 0° C., and after about 1 hour, the methanol was decanted. A honey-like, colorless product was obtained. This product was dissolved in hexane (150 mL) and washed three times with distilled water (50 mL). The solution was dried over $MgSO_4$ overnight. The $MgSO_4$ was filtered off, and the hexane was removed by a rotary evaporator. The completion of the hydrosilation and the structure of the product were determined by $^1$H NMR spectroscopy. Conversion of SiH via hydrosilation was about 83%, with provided about 33-40 g/mol of the desired poly[(anthracene protected 2-cyanoacryloxyalkyl) methylsiloxane-dimethylsiloxane] random copolymer. The yield was 75%.

The deprotection step is carried out as described above, by the retro Diels-Alder reaction. This procedure is similar to that in the literature. (*Unequivocal Synthesis of Bis(2-Cyanoacrylate) Monomers. I. Via Anthracene Adducts*, J. Polym. Sci.: Polym. Chem. Ed., Vol. 16, 2475-2507 (1978)), the disclosure of which is incorporated herein by reference. More particularly, 13.67 g (5.48 mmole of anthracene/allyl cyanoacrylate groups) of the poly[(anthracene protected 2-cyanoacryloxyalkyl) methylsiloxane-dimethylsiloxane]

was dissolved in 50 mL of freshly distilled xylene in a well dried 250 mL three neck round bottom flask equipped with a condenser and a magnetic stirrer. $SO_2$ inhibitor was bubbled into it for 30 minutes. The flask included 1.07 g (10.9 mmole) pulverized maleic anhydride and 57.5 mg $P_2O_5$. The mixture was stirred at reflux (about 140° C.) for about 8 hours, wherein the xylene was then distilled off. The remaining crude product was dissolved in 40 mL dry hexane. The anthracene/maleic anhydride adduct was then filtered and hexane was removed by distillation. The product, poly [(2-cyanoacryloxyalkyl) methylsiloxane-co-dimethylsiloxane], was a colorless greasy liquid. Conversion of the protected allyl cyanoacrylate to the allyl cyanoacrylate groups was 92%, equivalent to 7.8-9.5 poly[(2-cyanoacryloxyalkyl) methylsiloxane-co-dimethylsiloxane]. The yield was 95%.

In light of the foregoing, it should be clear that, by selecting the appropriate starting materials, a suitable silicone rubber containing cyanoacrylate functionalities can be provided. Such a product is particularly suitable for use as a wound closure. It will also be appreciated that the clinical characteristics, such as flexibility, curing time, etc., can be controlled by the judicious use of blends of the various compositions disclosed in the above six example schemes. Thus, various amounts of the products disclosed in Schemes 1 or 2 or 3 or 4 on the one hand can be blended with various amounts of the products disclosed in Schemes 5 or 6 on the other hand, and the blend applied to the wound. As these materials are chemically quite similar, they form homogeneous blends. The products in Schemes 1-4 are made with relatively high molecular weight PDMS (greater than 20.00 g/mol) so they will result in flexibilizing the wound closure; the products in Schemes 5 or 6 contain large amounts of CA groups and therefore will increase the rate of curing (set time) of the wound closure. Thus by selecting appropriate ratios of these groups of products the flexibility and curing time of the closure can be fine-tuned.

It will also be appreciated that the present invention can be used as wound closures or adhesives that can now be applied to skin that is in frequent motion, i.e., over the elbow, knee, knuckles, wrist, face, etc., in light of the fact that wound closures of the present invention are far more flexible or rubbery that contemporary wound closures. Furthermore, the present invention is oxygen permeable or breathable and, therefore, no longer serve as a barrier to oxygen necessary for healing of the skin. Still further, unlike contemporary cyanoacrylate-based wound closures and adhesives, the products of the present invention are not occlusive, meaning they allow the evaporation of water vapor caused by exudates within the wound during the healing process, which again, helps the healing of the wound. Also, the present invention may be used with or without additional layers as a wound closure or wound dressing. The present invention may also be used with or without foam dressings.

Although the present invention has been described in considerable detail with reference to certain embodiments, other embodiments are possible. Therefore, the spirit and scope of the appended claims should not be limited to the description of the embodiments contained herein.

What is claimed is:

1. A silicone rubber functionalized with at least one cyanoacrylate, and wherein at least one cyanoacrylate group is directly attached to the interior backbone of the silicone rubber.

2. The silicone rubber according to claim 1, wherein the silicone rubber is polydimethylsiloxane.

3. The silicone rubber according to claim 1, wherein the silicone rubber is functionalized with at least two cyanoacrylate groups.

4. The silicone rubber according to claim 3, wherein at least one other cyanoacrylate group is attached to a terminus end of silicone rubber.

5. A wound care product comprising the silicone rubber of claim 1.

6. The wound care product according to claim 5, wherein the wound care product is oxygen and water vapor permeable and flexible, and wherein the silicone rubber has a molecular weight of greater than or equal to 500 g/mol.

7. A silicone rubber functionalized along an interior backbone with at least one cyanoacrylate and a spacer group wherein the spacer group is oriented between the interior backbone and the cyanoacrylate group.

8. The silicone rubber according to claim 7, wherein the spacer group and cyanoacrylate group provide for a —CH2-CH2-CH2-CA substituent attached to the silicone rubber.

9. The wound care product according to claim 5 wherein the wound care product is attachable to skin as a wound closure, a wound adhesive, a wound sealant, or a skin protector.

10. The silicone rubber according to claim 7, wherein the spacer group is selected from a alkylene group and a polyalkylene oxide block.

11. A wound care product comprising the silicone rubber of claim 7.

12. The wound care product according to claim 11, wherein the wound care product is oxygen and water vapor permeable and flexible, and wherein the silicone rubber has a molecular weight of greater than or equal to 500 g/mol.

13. The wound care product according to claim 11 wherein the wound care product is attachable to skin as a wound closure, a wound adhesive, a wound sealant, or a skin protector.

14. A method for the preparation of a silicone rubber-containing polymer endowed with one or more functionalized cyanoacrylate groups, the method comprising:

reacting a polydimethylsiloxane terminated with a silane (—SiH), an anthracene/alkenyl 2-cyanoacrylate adduct having the formula wherein k is an integer from 1 to 16 and wherein the alkenyl 2-cyanoacrylate is protected, wherein the step of reacting includes hydrosilating the anthracene/alkenyl 2-cyanoacrylate adduct with each terminus end of the polydimethylsiloxane terminated with a silane, and wherein the reaction provides a silicone rubber endowed with at least one protected alkenyl 2-cyanoacrylate; and deprotecting the at least one anthracene-protected alkenyl 2-cyanoacrylate group with maleic anhydride to form the silicone rubber-containing polymer endowed with at least one functionalized cyanoacrylate group.

15. The method according to claim 14, wherein the step of deprotecting includes reacting the maleic anhydride with the at least one protected alkenyl 2-cyanoacrylate endowed on the silicone rubber, to form alkenyl 2-cyanoacrylate-terminated polydimethylsiloxane.

16. A method for the preparation of a silicone rubber-containing polymer endowed with one or more functionalized cyanoacrylate groups, the method comprising:

reacting a silicone rubber selected from the group consisting of (a) a methylhydrosiloxane-dimethylsiloxane diblock polymer, (b) a methylhydrosiloxane homopolymer, and (c) a methylhydrosiloxane-dimethylsiloxane random copolymer, with an anthracene/alkenyl 2-cyanoacryalte adduct having the formula wherein k is an integer from 1 to 16 and wherein the alkenyl 2-cyanoacrylate is protected, and wherein the step of reacting includes hydrosilating the anthracene/alkenyl 2-cyanoacrylate adduct with at least one SiH group present in the silicone rubber selected from ((a)) the methylhydrosiloxane-dimethylsiloxane diblock polymer, ((b)) the methylhydrosiloxane homopolymer, and ((c)) the methylhydrosiloxane-dimethylsiloxane random copolymer, and deprotecting the at least one anthracene-protected alkenyl 2-cyanoacrylate group with maleic anhydride to form the silicone rubber-containing polymer endowed with at least one functionalized cyanoacrylate group.

17. The method according to claim 16, wherein the step of deprotecting includes reacting the maleic anhydride with the at least one protected alkenyl 2-cyanoacrylate endowed on the silicone rubber, to form polydimethylsiloxane-b-poly[(2-cyanoacryloxyalkyl) methylsiloxane)] where the silicone rubber was the methylhydrosiloxane-dimethylsiloxane diblock polymer, poly(2-cyanoacryloxyalkyl methylsiloxane) where the silicone rubber was the methylhydrosiloxane homopolymer, and poly [(2-cyanoacryloxyalkyl) methylsiloxane-co-dimethylsiloxane] where the silicone rubber was the methylhydrosiloxane-dimethylsiloxane random copolymer.

* * * * *